United States Patent [19]

Materne et al.

[11] 4,277,483
[45] Jul. 7, 1981

[54] 1.4-DIHYDROPYRIDINE-DERIVATIVES WITH ANTIHYPERTENSIVE ACTIVITY

[75] Inventors: Carsten Materne, Bonn-Beuel; Hans Betzing, Kerpen-Horrem, both of Fed. Rep. of Germany

[73] Assignee: A. Nattermann & Cie. GmbH, Cologne, Fed. Rep. of Germany

[21] Appl. No.: 139,888

[22] Filed: Apr. 14, 1980

[30] Foreign Application Priority Data

Apr. 14, 1979 [DE] Fed. Rep. of Germany ....... 2915355

[51] Int. Cl.$^3$ .................... C07D 211/82; A61K 31/44
[52] U.S. Cl. ...................................... 424/263; 546/14
[58] Field of Search .......................... 546/14; 424/263

[56] References Cited

U.S. PATENT DOCUMENTS 3,485,847  12/1969  Bossert et al. ..................... 260/295.5
3,644,627  2/1972  Bossert et al. ....................... 424/266

*Primary Examiner*—John M. Ford
*Attorney, Agent, or Firm*—Schwartz, Jeffery, Schwaab, Mack, Blumenthal & Koch

[57] ABSTRACT

The present invention is related to the new 2.6-dimethyl-4-(3'-nitrophenyl)-1.4-dihydropyridine-3-carboxylic acid beta-trimethylsilylethyl ester-5-carboxylic acid lower alkyl esters with improved antihypertensive and to a process for the treatment of humans suffering from hypertension with such compounds.

6 Claims, No Drawings

1.4-DIHYDROPYRIDINE-DERIVATIVES WITH ANTIHYPERTENSIVE ACTIVITY

It is known that 1.4-dihydropyridine-3.5-dicarboxylic acid esters have vasodilatatory and antihypertensive activity (see for instance German Pat. No. 1 670 827 or F. Bossert and W. Vater, Naturwissenschaften vol. 58 (1971) p. 578).

It has now been found that the introduction of the trimethylsilyl group into one of the ester groups yields into 1.4-dihydropyridine derivatives with increased antihypertensive activity and without a coronary and cerebraldilatatory activity.

The new 1.4-dihydropyridine derivatives according to the present invention with improved antihypertensive activity are the 2.6-dimethyl-4-(3'-nitrophenyl)-1.4-dihydropyridine-3-carboxylic acid beta-trimethylsilylethyl ester-5-carboxylic acid lower alkyl esters wherein the lower alkyl group are straight or branched alkyl groups having from 1 to 4 carbon atoms. The compounds corresponds to the general formula I

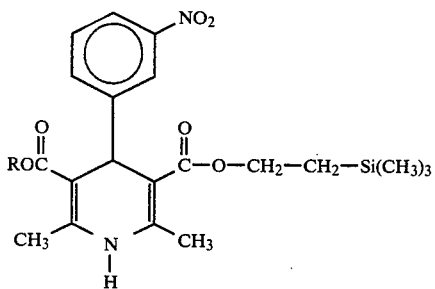

wherein R is a straight or branched alkyl group having from 1 to 4 carbon atoms.

The new compounds according to the present invention with improved antihypertensive activity produce a decrease of the systolic blood pressure of 20 to 30 mm Hg in the anesthetized dog when administered in dosages of 0.1 to 1 mg per kg intravenously. The same dosage range applies to humans.

The new 1.4-dihydropyridine derivatives according to the present invention may be produced in manners known per se for similar compounds of this group of products. Thus, 3-aminocrotonic acid beta-trimethylsilylethyl ester is subjected to reaction with meta-nitro-benzylidene acetic acid lower alkyl esters of the general formula II

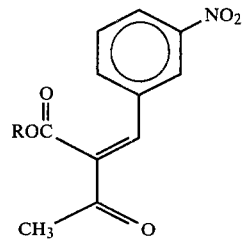

wherein the alkyl group R is identical with the alkyl group in the new 1.4-dihydropyridine derivatives according to the present invention, the reaction being carried out in an organic solvent such as an alcohol, dioxane, acetic acid ester, anhydrous acetic acid, dimethylformamide or acetonitrile. Preferably, the reaction is carried out at a temperature ranging from 20° to 150° C., most preferably at the boiling point of the reaction solution. The products used as starting materials, as above indicated, are known as such or may been produced by manners known per se.

The following examples serve to further illustrate the present invention without however limiting the same thereto.

EXAMPLES 2.6-Dimethyl-4-(3'-nitrophenyl)-1.4-dihydropyridine-3-carboxylic acid beta-trimethylsilylethyl ester-5-carboxylic acid isopropyl ester is obtained by subjection 5.5 g of 3-aminocrotonic acid beta-trimethylsilylethyl ester and 7.6 g of meta-nitro-benzylidene acetic acid isopropyl ester dissolved in a mixture of 30 ml of ethanol and 10 ml of glacial acetic acid, to heating at 100° C. for 3 hours. The resulting solution is evaporated to dryness and the resulting product is purified (adsorption to silicic acid gel, chloroform). Thus, 2.3 g of the desired final product (yield: 25 percent of the theoretical) is obtained. Melting point: 100° C.

Starting from the appropriate meta-benzylidene acetic acid alkyl esters, the following products according to the present invention are produced in a similar manner:

2.6-Dimethyl-4-(3'-nitrophenyl)-1.4-dihydropyridine-3-carboxylic acid beta-trimethylsilylethyl ester-5-carboxylic acid methyl ester. Melting point: 140° C.

2.6-Dimethyl-4-(3'-nitrophenyl)-1.4-dihydropyridine-3-carboxylic acid beta-trimethylsilylethyl ester-5-carboxylic ethyl ester. Melting point: 122° C.

What we claim is:

1. The 2.6-dimethyl-4-(3'-nitrophenyl)-1.4-dihydropyridine-3-carboxylic acid beta-trimethylsilylethyl ester-5-carboxylic acid lower alkyl esters wherein the lower alkyl group is a straight or branched alkyl group from 1 to 4 carbon atoms.
2. 2.6-Dimethyl-4-(3'-nitrophenyl)-1.4-dihydropyridine-3-carboxylic acid beta-trimethylsilylethyl ester-5-carboxylic acid isopropyl ester.
3. 2.6-Dimethyl-4-(3'-nitrophenyl)-1.4-dihydropyridine-3-carboxylic acid beta-trimethylsilylethyl ester-5-carboxylic acid ethyl ester.
4. 2.6-Dimethyl-4-(3'-nitrophenyl)-1.4-dihydropyridine-3-carboxylic acid beta-trimethylsilylethyl ester-5-carboxylic acid methyl ester.
5. Process for the treatment of a human suffering from hypertension comprising administering to him a 2.6-dimethyl-4-(3'-nitrophenyl)-1.4-dihydropyridine-3-carboxylic acid beta-trimethylsilylethyl ester-5-carboxylic acid lower alkyl ester according to claim 1.
6. Process according to claim 5 wherein the ester is administered in an amount corresponding to 0.1 to 1 mg. per kg.